(12) United States Patent
Kissinger et al.

(10) Patent No.: US 6,545,187 B1
(45) Date of Patent: Apr. 8, 2003

(54) PRODUCTION OF LOW-PARTICULATE BISPHENOL AND USE THEREOF IN THE MANUFACTURING OF POLYCARBONATE

(75) Inventors: Gaylord Michael Kissinger, Evansville, IN (US); Fang Christine Chen, Evansville, IN (US); James Cristopher Blubaugh, Evansville, IN (US); Darlene Hope Nance, Mt. Vernon, IN (US); Edward Brittain Stokes, Schenectady, NY (US); Juan Rodriguez Ordonez, Madrid (ES); Jose M. Quintana, Murcia (ES)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/682,560

(22) Filed: Sep. 19, 2001

(51) Int. Cl.$^7$ ................................................ C07C 37/68
(52) U.S. Cl. ...................... 568/724; 528/196; 422/190
(58) Field of Search ................................ 568/724, 727, 568/728; 528/196; 422/190

(56) References Cited

U.S. PATENT DOCUMENTS

| | | |
|---|---|---|
| 4,107,218 A | 8/1978 | Konrad et al. |
| 4,294,994 A | 10/1981 | Li |
| 4,447,655 A | 5/1984 | Mendiratta |
| 4,798,654 A | 1/1989 | Iimuro et al. |
| 4,931,146 A | 6/1990 | Iimuro et al. |
| 5,210,329 A | 5/1993 | Gomes de Matos et al. |
| 5,243,093 A | 9/1993 | Kissinger et al. |
| 5,245,088 A | 9/1993 | Fimuro et al. |
| 5,288,926 A | 2/1994 | Patrascu et al. |
| 5,368,827 A | 11/1994 | Moriya et al. |
| 5,786,522 A | 7/1998 | Cipullo |
| 5,874,644 A | 2/1999 | Gammill |
| 6,008,315 A | 12/1999 | Kimura et al. |
| 6,197,917 B1 | 3/2001 | Kimura et al. |
| 6,204,352 B1 | 3/2001 | Kimura et al. |

*Primary Examiner*—Michael L. Shippen
(74) *Attorney, Agent, or Firm*—Oppedahl & Larson LLP

(57) ABSTRACT

Low-particulate dihydric aromatic compounds such as bisphenol-A that can be used in the synthesis of low-particulate polycarbonates are prepared by introducing into a desorber column containing a non-aggregate packing material an adduct of bisphenol and phenol and optionally a stripping gas. The column is maintained at an operating temperature that is sufficiently high and an operating pressure that is sufficiently low such that the adduct is distilled. The stream of phenol and the stripping gas is recovered from the top of the column. A second stream containing bisphenol that is substantially free of added particulate matter is recovered from the bottom of the column. This purified stream of bisphenol-A can further be used in a method of producing optical-grade polycarbonate.

39 Claims, 4 Drawing Sheets

PRODUCTION OF LOW-PARTICULATE BISPHENOL AND USE THEREOF IN THE MANUFACTURING OF POLYCARBONATE

BACKGROUND OF INVENTION

The present invention relates to the production of low particulate bisphenols and to the use of such bisphenols in the manufacturing of high-quality, low-particulate polycarbonates intended for optical-grade products.

There are two common methods for manufacturing polycarbonates, the interfacial method and the melt polycondensation method. The interfacial method involves the reaction of a dihydric aromatic compound with a carbonyl halide, such as between bisphenol-A and phosgene. A primary disadvantage of the interfacial method is the use of phosgene and the use of a large amount of solvent. The melt polycondensation method uses a transesterification reaction between a dihydric aromatic compound and a diester of carbonic acid, such as diphenyl carbonate. The melt method avoids the disadvantages of the interfacial method and also eliminates chlorine from the process which is desirable because chlorine can lead to a less consistent color in the polycarbonate.

Bisphenol-A is the preferred dihydric compound in the synthesis of polycarbonate, and as such, much attention has been directed at developing methods for the purification of bisphenol-A. U.S. Pat. No. 4,447,655 describes a method for the purification of bisphenol-A through the use of a water/bisphenol-A crystal slurry. U.S. Pat. No. 4,798,654 is directed at a distillation column whereby recycling of the distillate leads to purified bisphenol-A. U.S. Pat. No. 4,931,146 involves the purification of bisphenol-A with steam-stripping in a multi-tubular packed column. In general, processes for the production and purification of bisphenols are well known, and are described inter alia in U.S. Pat. Nos. 4,107,218; 4,294,994; 5,210,329; 5,243,093; 5,245,088; 5,288,926; 5,368,827; 5,786,522; and 5,874,644.

High quality polycarbonate that has low levels of particulate matter is desirable in the manufacturing of DVD"s, CD-ROM"s, ophthalmic lenses, or other optical-grade products. The micron-sized particles that can be introduced in the process of manufacturing polycarbonate have the undesirable effect of scattering light. In the case of optical disks, this scattering of light introduces noise. Therefore, methods of removing these particulates is extremely desirable and several patents are consequently directed at this objective.

U.S. Pat. No. 6,008,315 discloses a method for producing bisphenol-A that has low-particulate impurities by using a calcined metal filter. U.S. Pat. No. 6,197,917 discloses the use of a fluorine resin membrane to filter micron-sized particles from a molten mixture of bisphenol-A with a carbonic diester. Combining the bisphenol-A and carbonic diester increases the efficiency of filtering with the fluorine resin membrane.

A different approach to eliminating particulates in the manufacturing of polycarbonate via the melt polycondensation method is disclosed in U.S. Pat. No. 6,204,352. In this process, the entire apparatus that is used in the synthesis of the polycarbonate is made of various alloys of nickel or stainless steel. These alloys were developed to prevent the discoloration of polycarbonate and further refined to eliminate the presence of metallic particulates in the polycarbonate.

SUMMARY OF INVENTION

The present invention relates to a method of producing a low-particulate bisphenol-A stream that can be used in the synthesis of polycarbonate. The method comprises the following steps:(a) introducing into a desorber column containing a non-aggregate packing material an adduct of a dihydric aromatic compound and phenol;(b) providing an operating temperature range in the desorber column that is sufficiently high and an operating pressure in the column that is sufficiently low such that the adduct is distilled;(c) discharging from the desorber column a first stream containing substantially all of the phenol; and(d) discharging from the desorber column a second stream containing substantially all of the dihydric aromatic compound; whereby the second stream is substantially free of added particulate matter as compared to the adduct stream introduced to the column. The invention can be applied in the context of a vacuum distillation column, or may utilize a stripping gas which is introduced in countercurrent flow relative to the adduct. The resulting stream of dihydric aromatic compound can further be used in a method of producing optical-grade polycarbonate.

DETAILED DESCRIPTION

Figure 1:
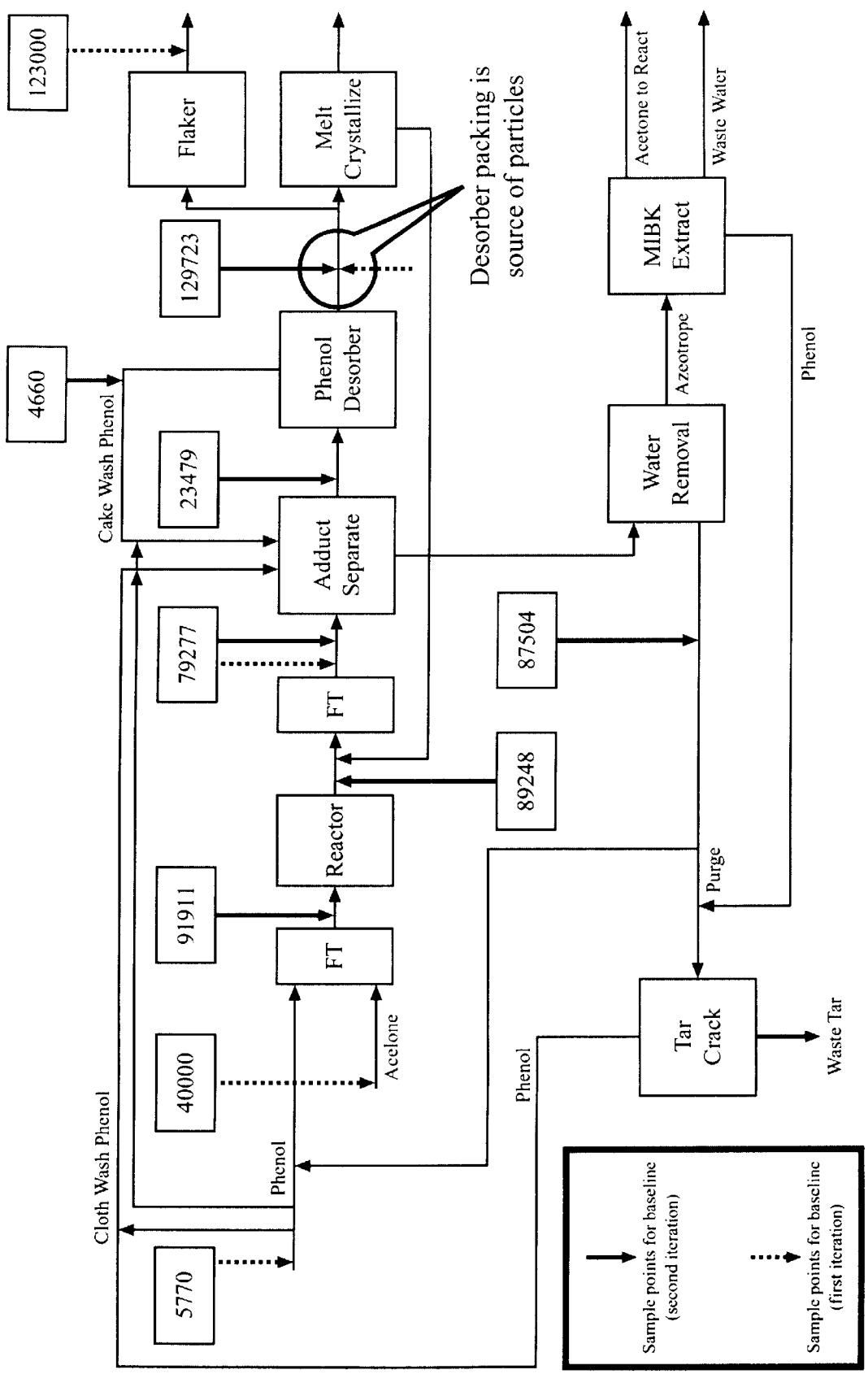
FIG. 1 shows a schematic representation of a bisphenol-A plant in accordance with the art, with particulate levels at various points in the process indicated.

The present invention relates to the preparation of polycarbonate, and to the control of levels of particulate materials in polycarbonate products. It will be appreciated that in any process for manufacturing polycarbonates there may be various sources of particulates. The present invention is directed to addressing only one of these sources. Thus, the present invention is directed towards the production of high-quality polycarbonate that is substantially free of particulate matter derived from the bisphenol component of the reaction mixture used in forming the polycarbonate through the use of a bisphenol product with low particulate levels.

Bisphenol having low particulate levels can be prepared by a method according to the invention for producing purified bisphenol that comprises the steps of:(a) introducing into a desorber column possessing a non-aggregate packing material an adduct of a dihydric aromatic compound and phenol;(b) providing an operating temperature range in the desorber column that is sufficiently high and an operating pressure in the column that is sufficiently low such that the adduct is distilled;(c) discharging from the column a first stream consisting essentially of phenol; and(d) discharging from the desorber column a second stream containing substantially all of the dihydric aromatic compound. The second stream is substantially free of added particulate matter, as compared to the introduced adduct, and can be used in a method of producing optical-grade polycarbonate.

The method of the invention can be practiced in a vacuum distillation column with packed section. Alternatively, the invention may be practiced using a stripping gas. In this case, the stripping gas is introduced in countercurrent flow relative to the adduct and is substantially recovered as part of the second stream.

There are no particular restrictions on the dihydric aromatic compound that can be used in the production of the high-quality polycarbonate and numerous species of dihydric aromatic compounds are known for this purpose in the art. For example, a bisphenol having structure I may be used:

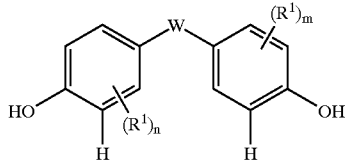

wherein $R^1$ is independently at each occurrence a halogen atom, nitro group, cyano group, $C_1$–$C_{20}$ alkyl group, $C_4$–$C_{20}$ cycloalkyl group, or $C_6$–$C_{20}$ aryl group; n and m are independently integers 0–3; and W is a bond, an oxygen atom, a sulfur atom, a $SO_2$ group, a $C_1$–$C_{20}$ aliphatic radical, a $C_6$–$C_{20}$ aromatic radical, a $C_6$–$C_{20}$ cycloaliphatic radical or the group

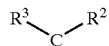

wherein: $R^2$ and $R^3$ are independently a hydrogen atom, $C_1$–$C_{20}$ alkyl group, C C cycloalkyl group, or C C aryl group; or $R^2$ and $R^3$ together form a C $C_{20}$ cycloaliphatic ring which is optionally substituted by one or more $C_1$–$C_{20}$ alkyl, $C_6$–$C_{20}$ aryl, $C_5$–$C_{21}$ aralkyl, $C_1$–$C_{20}$ cycloalkyl groups or a combination thereof. Suitable bisphenols I for use in the method of the present invention include bisphenol-A; 2,2-bis(4-hydroxy-3-methylphenyl)propane; 2,2-bis(3-chloro-4-hydroxyphenyl)propane; 2,2-bis(3-bromo-4-hydroxyphenyl)propane; 2,2-bis(4-hydroxy-3-isopropylphenyl)propane; 1,1-bis(4-hydroxyphenyl)cyclohexane; 1,1-bis (4-hydroxy-3-methylphenyl)cyclohexane; and 1,1-bis(4-hydroxyphenyl)-3,3,5-trimethylcyclohexane.

The dihydric aromatic compound which is produced and used in the invention may also be a modified (i.e., functionalized) compound. For example brominated bisphenols may be used to introduce bromine into the final polycarbonate to reduce flammability.

FIG. 1 shows a schematic representation of a bisphenol plant using alumina (Coors AD995, 99.5% alumina) packing in the phenol desorber column. Measurements of particle levels were taken at the points indicated by the arrows, and the measurement amounts of particulates in the 0.5 to 50 μm size range per gram of sample are indicated in the adjacent boxes. As shown, the alumina desorber column is a significant source of particulates. Subsequent studies conducted in connection with the present invention established that silica, alumina and magnesium packing materials conventionally used as column packing for the separation of bisphenol:phenol adducts all undergo deterioration, giving rise to increased levels of undesirable particulates in the product bisphenol stream. The precise mechanism for this deterioration is not known, although it presumably arises from thermal shocking, chemical corrosion, mechanical friction, or some combination thereof. Regardless of the mechanism, the deterioration was readily observable in a 6,000×scanning electron micrograph (SEM) of the surface of a used alumina ceramic ball. The micrograph showed a highly textured surface, with structures on the order of 1 μm in size, reminiscent of a coral-encrusted ocean floor. The surface fragility of alumina ceramic balls was further reflected in a 10,000×SEM of the surface of an ultrasonified alumina ceramic ball. In this case, the surface was covered with broken-up chunks, having sizes on the order of 2 μm. The present invention reduces the amount of added particles at this stage in the process through the selection of "non-aggregate" packing materials which are less susceptible to these factors as a result of their physical structure.

As used in the specification and claims of this application, the term "non-aggregate packing material" refers to a non-polycrystalline material that is substantially devoid of grain-boundary regions that are subject to separation or fracture under the conditions of temperature and pressure found in the desorber column. It will be appreciated that the term "non-aggregate" does not mean that there are no locations where focused fracture might occur under more extreme conditions. Lacking weak (in the context of the desorber column conditions) grain-boundary regions and an "aggregate" of micro-crystals, "non-aggregate" materials are not susceptible to the exfoliation of microscopic crystalline matter under the conditions found in the desorber column. Examples of non-aggregate material include borosilicate glass, stainless steel, zirconia, and polytetrafluoroethylene. A preferred embodiment of the present invention utilizes borosilicate glass as the column packing.

Use of non-aggregate substance as a packing material in the column leads to the production of bisphenol that is substantially free of added particulate matter. The amount of particles in a bisphenol preparation can be determined by various techniques including analytical particle counter instruments such as a Hiac-Royco Particle Counter. As used in the specification and claims of this application, the term "substantially free of added particulate material" refers to bisphenol preparations which contain on average less than 50,000 added particles/gm of bisphenol product having a size of 0.5 to 50 μm, more preferably less than 20,000 added particles/gm, as determined by the technique described in Example 1 below. Thus, the method of the present invention can lead to at least an 80% reduction of particulate matter in a stream of bisphenol-A as compared to methods employing columns packed with alumina or silica.

The selection of the column in accordance with the invention is not specifically intended to reduce the amount of particulates which may be present in the reactant streams introduced to the desorber column. Rather, the invention addresses particles which are added during the separation of bisphenol from phenol as a result of the nature of the column packing, and thus provides bisphenol which is substantially free of added particles, rather than bisphenol having particulate levels below any specific threshold. To maintain the overall quality of the bisphenol product it may be desirable to include filters positioned downstream from the bisphenol reactor, upstream from the bisphenol reactor or both to capture particulates which may be derived from other sources. Such filters may, for example, be fluorine resin membranes or calcined metal filters as known in the art.

To practice the method of the present invention, a column is charged with a non-aggregate packing material. The packing material may be of any shape, such as without limitation spheres, saddles, or Raschig or Pall rings, and be of any size, without limitation, that is currently known in the art. The selected packing material should have a void volume such that, at the flow rate of gas employed, the column operates with fluid at the top of the column. Furthermore, in the case of denser packing materials, such as stainless steel, it is desirable to use hollow balls to avoid undue weight on the column. The column itself may suitably be made of stainless steel, for example 316 or 304 stainless, or glass, or it may be glass lined. Column materials which are themselves sources of particulates are suitably avoided.

Figure 2:
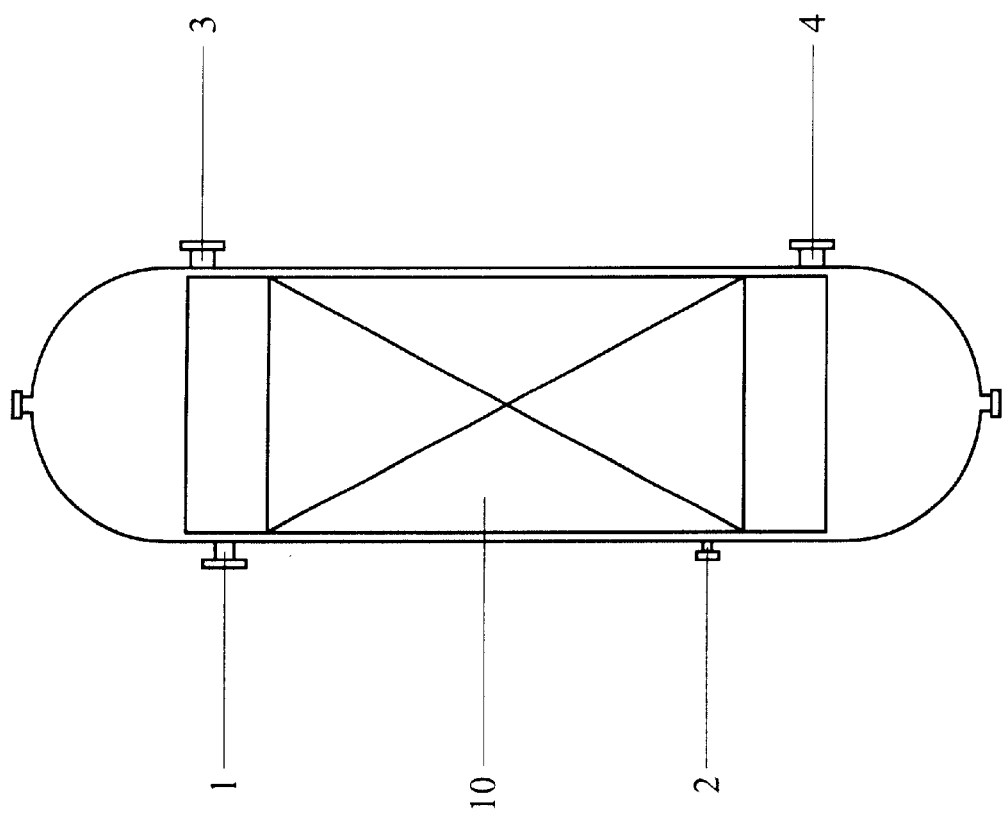
FIG. 2 shows a column charged with a borosilicate packing material that can be used for the distillation of an adduct of a dihydric aromatic compound and phenol.

As shown in FIG. 2, the column 10 has a first inlet 1 for introducing an adduct containing, for example, phenol and a dihydric compound such as bisphenol-A, and a second inlet 2 for introducing nitrogen or some other stripping gas such as argon, helium, nitrogen, carbon dioxide or steam. The stripping gas operates in a counter-current mode where the flow of the stripping gas is opposite to the adduct flow. To remove the distillation products, the column 10 possesses a first outlet 3 at the top of the column to remove a stream containing the stripping gas and phenol, and a second outlet 4 at the bottom of the column to remove a stream containing substantially particle-free bisphenol-A.

The adduct is appropriately introduced to the column 10 at an elevated temperature to minimize thermal disruption of the distillation system. Suitably, this temperature is in the range of from about 95 to 220° C., more preferably from 150 to 180° C. The stripping gas may be introduced at ambient temperature (i.e., around 20–25° C.), or may be pre-heated to a temperature comparable to the temperature at the bottom of the column, for example up to 220° C. The adduct and stripping gas are introduced at rates that account for the dimensions of the column, namely volume and length; the volume, shape and flow properties of the packing material; and, in general, operating pressure and the rate of distillation of the adduct (i.e., the removal of distillation products from the column).

The rate of distillation of the adduct is dependent upon the temperature and pressure maintained in the column and the boiling point properties of the adduct. In general, the adduct has a nominal phenol to bisphenol ratio, but also has additional phenol because it is in the form of a wet cake that is wet with phenol. The amount of wetting phenol can be such that the actual ratio of phenol to bisphenol-A in a wet nominally 1:1 adduct cake is in the range of 45–70.8% BPA and 29.2–55% phenol, rather than the theoretical composition of 70.8%BPA and 29.2% phenol. For distilling an adduct of phenol and bisphenol-A in a nominal 1:1 ratio (regardless of the amount of additional phenol), distillation occurs when the temperature at the bottom of the column is about 185° C. and the pressure of the column is maintained at 760 mm of Hg. Decreasing the pressure in the column to below atmospheric pressure allows for distillation to occur at a lower temperature and increases the capacity of the column. The pressure can be regulated by using a liquid ring pump to collect gas from the top of the desorber column. The operating parameters of the pump are balanced against the input flow rate of gas to the bottom of the desorber column to achieve the desired pressure. The column pressure may be maintained between a range of about 35 to about 810 mm Hg and the temperature adjusted accordingly to maintain the distillation of the adduct. Reduced gas flow is generally required when pressure is decreased to maintain separation efficiency. For reduced pressure operation, the pressure is suitably in the range of 35 to 750 mm Hg, more conventionally 250 to 750 mm Hg. Assuming near atmospheric pressure, the temperature of the column is maintained at a range (from the top of the column to the bottom) of about 170 to about 220° C. The ideal distillation rate is achieved by maximizing the production of bisphenol-A, but minimizing the concentration of phenol in the bisphenol-A stream.

Distillation in the desorber column of the invention produces two streams, one containing substantially all of the phenol and one containing substantially all of the bisphenol. While it will be appreciated that the ordinary goal of the desorber column is to achieve the maximum degree of separation, for purposes of the specification and claims of this application, a stream which contains "substantially all" of the bisphenol or phenol will be one which contains at least 80% of the identified component from the adduct.

After producing the stream of low-particulate dihydric aromatic compound, the dihydric aromatic compound is used in the production of polycarbonate using either the interfacial method or the melt polycondensation method. Thus, the present invention contemplates a reaction of the purified bisphenol-A with a derivative compound of carbonic acid, namely either carbonyl chloride (phosgene) or any other carbonic diester known in the art, such as those disclosed in U.S. Pat. No. 6,204,352. Specific examples of carbonic diesters that can be used in the transesterification reaction, either alone or in combination with one another, include diphenyl carbonate, bis(methyl salicyl) carbonate, ditolyl carbonate, bis(chlorphenyl) carbonate, m-cresyl carbonate, dinaphthyl carbonate, bis(diphenyl) carbonate, diethyl carbonate, dimethyl carbonate, dibutyl carbonate and dicyclohexyl carbonate. Of these, diphenyl carbonate is particularly favorable.

The method of the invention may be practiced in a facility for separation of an adduct of a dihydric phenol and phenol into separate streams of dihydric phenol and phenol, comprising a source of the adduct and a desorber column connected to the source of adduct in which the desorber column is packed with a non-aggregate packing material such as borosilicate galls, stainless steel, zirconia and polytetrafluoroethylene. The facility may include a source of stripping gas, for example, nitrogen, carbon dioxide or steam, connected to the desorber column to introduce stripping gas in counter-current flow to the adduct. The facility may also include a ring pump connected to the desorber column for maintaining sub-atmospheric pressure in the desorber column during operation.

In the course of considering the benefits of the present invention in reducing particulates, it was noted that the same result might be achieved not through an actual reduction in particulates but through the formation of particulates which were effectively invisible in polycarbonate as a result of having the same refractive index. To explore this possibility, we looked at the refractive indices of various materials, as summarized in. Table 1. The refractive index for polycarbonate was taken to be 1.586. As is apparent from the difference in refractive indices, the absence of measurable particles using borosilicate cannot be attributed to an invisibility phenomenon. Nevertheless, if a column material were identified which had the correct refractive index, this would serve as an alternative approach to reduction of particulates in bisphenol and resulting polycarbonate, even if the column material were subject to deterioration.

TABLE 1

| Material | Refractive Index | Difference from PC |
| --- | --- | --- |
| alumina | 1.76 | 0.174 |
| silica | 1.55 | −0.036 |
| borosilicate (Sigmund Lindner Type 3.3) | 1.473 | −0.113 |

The invention will now be described further with reference to the following non-limiting examples.

EXAMPLE 1

A column (packed column length 13 feet-7-9/16 inches, interior diameter 10") was initially charged with about 5 to 6 ft³ (or about 200 to 250 kg) of alumina balls as a packing material. After a period of operation, the alumina balls were replaced with the same volume of comparably-sized borosilicate glass balls. Throughout operation with either type of packing material, nitrogen and a 1:1 adduct of bisphenol-A:phenol were introduced in a countercurrent flow. The adduct was fed into the column at a temperature of about 135° C. and a rate of 0.44 gpm. The gas flow rate of nitrogen was about 28 scfm/ft of surface area of the column. The pressure of the column was maintained at about 760 mm Hg. The temperature of the bottom of the column was about 185° C., while the temperature of the top of the column was: about 180° C.

Samples were taken periodically from the feed material and the desorber column bottoms for particulate analysis. Samples were caught in 16 ounce clean room prepared jars. About 20 g of sample was caught in each jar. To this was added about 238 grams of HPLC grade methanol. The exact amount of methanol needed was determined as equal to grams of sample/(20/238). Particulates having a size of from 0.50 to 50.0 μm are counted in each sample with a Hiac-Royco portable particle counter. Blanks of HPLC-grade methanol were run prior to the sample and between each sample. The particle count in the blanks was from 2,000 to 5,000 total particles.

Figure 3:
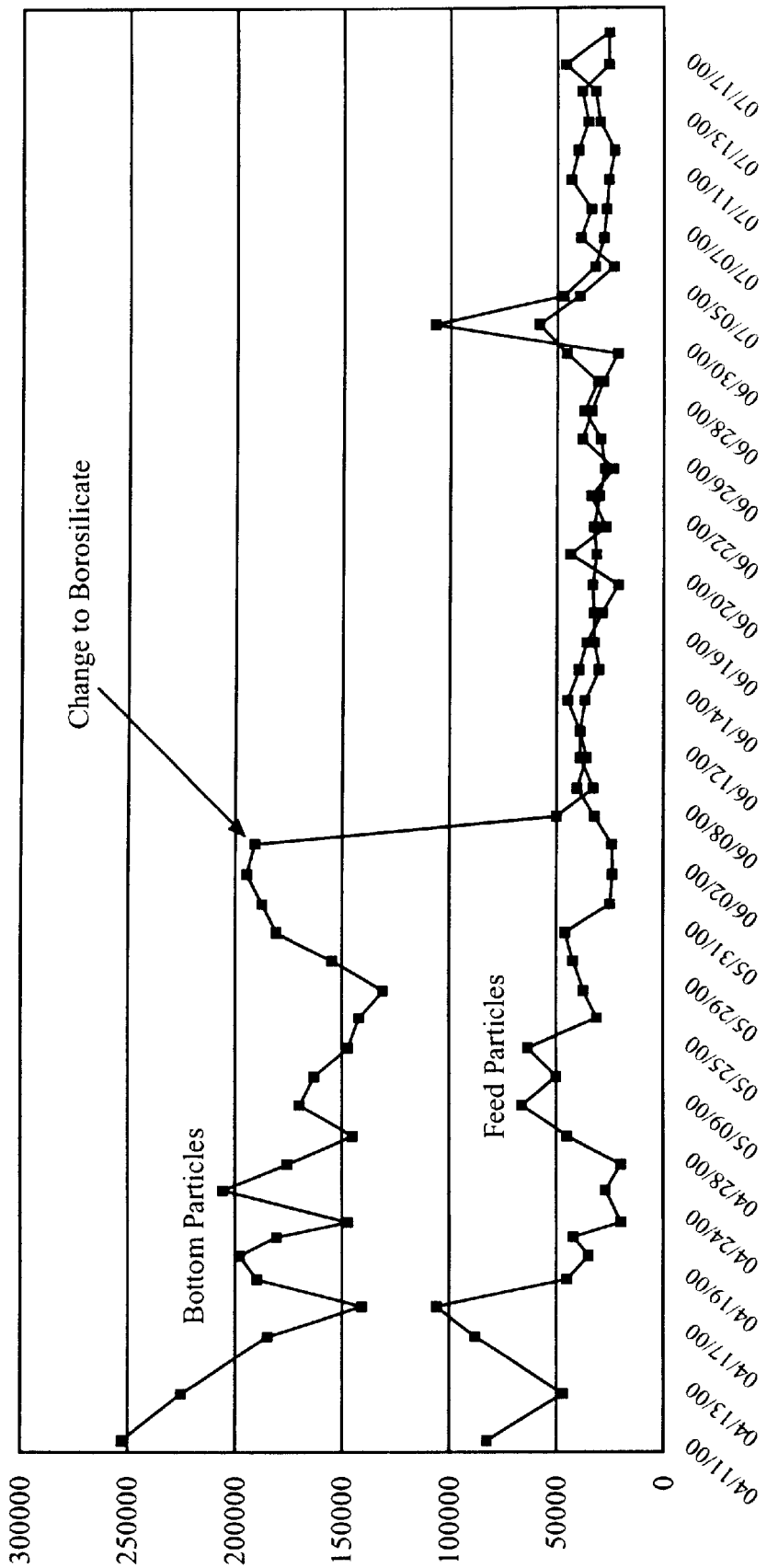
FIG. 3 shows particulate levels in feed and bottoms samples from a pilot scale desorber column with two types of packing.
Figure 4:
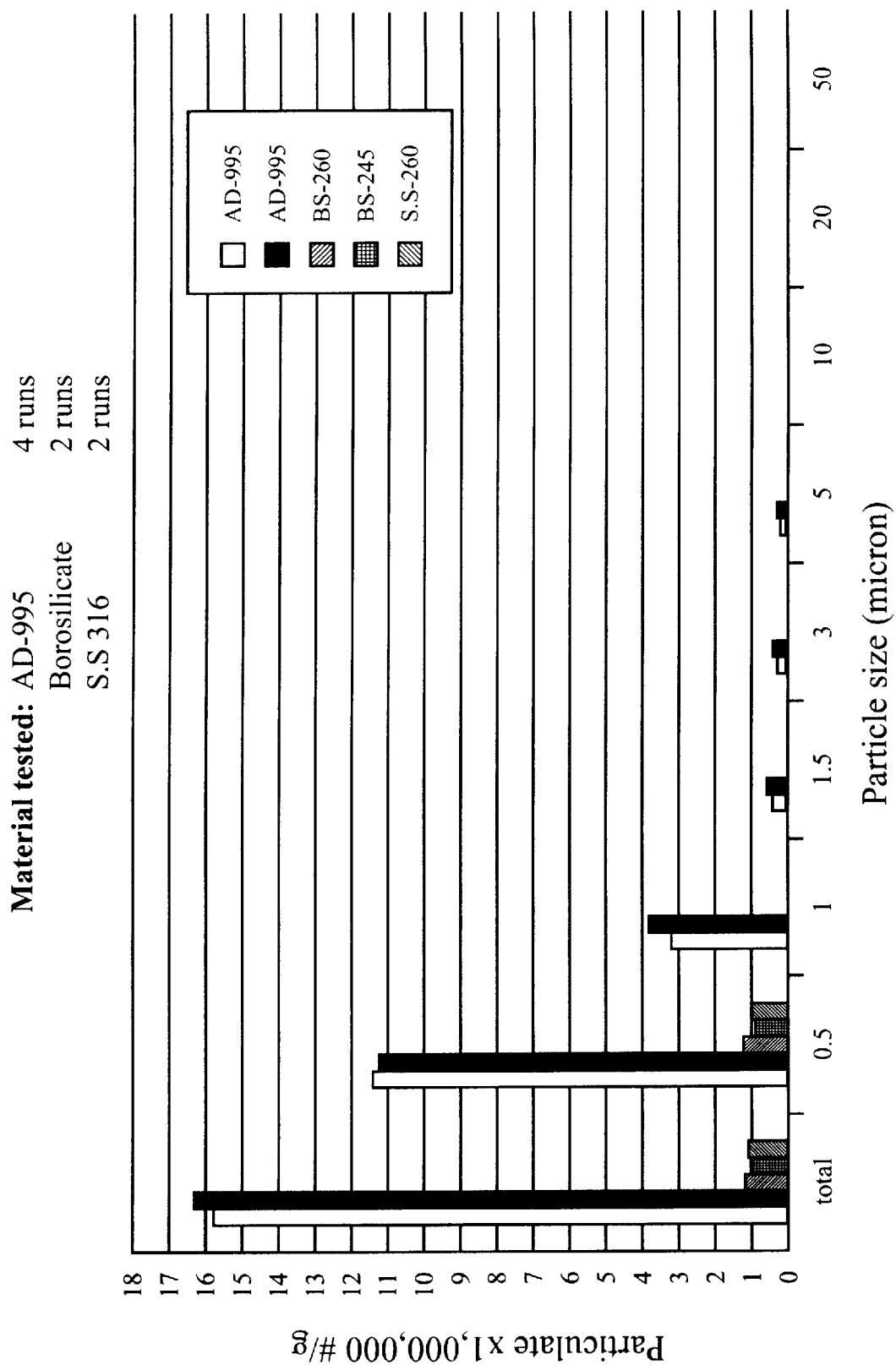
FIG. 4 shows particle counts as a function of particle size for several types of packing material.

FIG. 3 shows a comparison of the particulate levels in the bottoms (—squares—) as compared to the feed (—diamonds—) before and after the change in packing material. As shown, there is a substantial increase in the particulate level in the column bottoms using the ceramic packing material. On the other hand, the bottoms samples obtained after the change to borosilicate glass packing have essentially no added particulates.

Measurement on the quality of the product also showed an interesting and unexpected improvement. During the portion of the run with the alumina ceramic balls, the residual phenol level was 56 ppm, while the residual isopropenyl phenol (IPP) level was 53 ppm. In contrast, when borosilicate packing material was used, the levels were 34 and 41 ppm respectively. Thus, changing the packing results not only in reduced particulate levels, it also improves the separation efficiency and reduces levels of side-reaction products.

EXAMPLE 2

Bench scale tests were conducted in a 1 liter 3 neck flask. The flask was heated with a mantle connected to a variable power supply. A condenser was used to condense the phenol as it vaporized during the experiment. Temperature control was accomplished by first allowing the phenol to pass through the condenser and then, when the desired boiling temperature was reached, starting a 45° C. water flow through the condenser jacket to begin total reflux. A temperature probe was used to get the actual liquid temperature in the flask.

To simulate conditions of high thermal stress, packing material was placed into the flask with an amount of liquid material such that the packing was only partially immersed in the boiling mixture (240–255° C.). The exposed portion of the packing comes into contact with the cooler phenol condensate spilling down from the reflux condenser, thus simulating "thermal shock" which could lead to deterioration of the packing.

A phenol/BPA mixture (roughly a 1:2 ratio) was used in each experiment. The phenol/BPA mixture was added to the flask and melted. After melting, a sample A was taken. The packing material was then added to the flask and the temperature increased to the desired temperature for the experiment. After the boiling point was reached, another sample B was taken. Condenser water was applied to start the reflux which was maintained for 2 hours. At the end of this time, a final sample C was taken. Table 2 summarizes the experimental conditions and the observed results. The "total particulates" is calculated as the amount of particles per gram in sample C minus the sum of the particulates in samples A and B. As can be seen, the amount of added particulates is much less in the case of the borosilicate glass packing material than in the AD995 alumina ceramic (Coors) used as a comparison. The amounts of particulates are also higher than those observed in the actual packed column tests, suggesting that the thermal stresses in the bench test are more extreme than those which actually occur in the column.

TABLE 2

| Column Packing | Temp (° C.) | weight percent phenol/BPA | Total Particulates |
|---|---|---|---|
| None | 255 | 30.83/69.17 | 109,610 |
| alumina (Run 1) | 240 | 35.33/64.67 | 15,638,525 |
| alumina (Run 2) | 240 | 33.20/66.80 | 16,291,480 |
| Borosilicate (Run 1) | 251 | 38.68/61.32 | 566,960 |
| Borosilicate (Run 2) | 245 | 33.94/66.06 | 1,210,536 |

EXAMPLE 3

Zirconia balls were tested as packing material. The total particulates observed (C–B) was 1,454,965 particles per gram.

EXAMPLE 4

Packing balls sold under the tradename CHIPTON ($Al_2O_3$=13–17%; $SiO_2$=74–78%; $Na_2O$ 2.5%; $B_2O_3$=not detected; MgO=0.5%; other =5.5% were tested as packing material. The total particulates observed (C–B) was 1,086,950 particles per gram.

What is claimed is:

1. A method of producing a low-particulate dihydric aromatic compound, comprising the steps of:
    (a) introducing into a desorber column possessing a non-aggregate packing material an adduct of a dihydric aromatic compound and phenol;
    (b) providing an operating temperature range in the desorber column that is sufficiently high and an operating pressure in the column that is sufficiently low such that the adduct is distilled;
    (c) discharging from the desorber column a first stream containing substantially all of the phenol; and
    (d) discharging from the desorber column a second stream containing substantially all of the dihydric aromatic compound; whereby the second stream is substantially free of particulate matter added in the desorber column.

2. The method of claim 1, wherein the non-aggregate packing material is selected from the group consisting of borosilicate glass, stainless steel, zirconia, and polytetrafluoroethylene.

3. The method of claim 1, wherein the non-aggregate packing material is made from borosilicate glass.

4. The method of claim 1, wherein a stripping gas is introduced to the column in countercurrent flow to the adduct.

5. The method of claim 4, wherein the stripping gas is selected from the group consisting of nitrogen, carbon dioxide and steam.

6. The method of claim 4, wherein the dihydric aromatic compound is a bisphenol.

7. The method of claim 4, wherein the dihydric aromatic compound is bisphenol-A.

8. The method of claim 7, wherein the operating temperature range in the column is about 172 to about 217° C.

9. The method of claim 8, wherein the operating pressure of the column is in a range from about 35 trout 810 mm Hg.

10. The method of claim 4, wherein the operating temperature range in the column is about 172 to about 217° C.

11. The method of claim 10, wherein the operating pressure of the column is in a range from about 35 to about 810 mm Hg.

12. The method of claim 4, wherein the operating pressure of the column is in a range from about 35 to about 810 mm Hg.

13. The method of claim 4 wherein the operating pressure of the column is below atmospheric pressure.

14. The method of claim 1, wherein less than 20,000 particulates per gram of bisphenol are added in the desorber column.

15. A method of manufacturing low-particulate polycarbonate, comprising the steps of:
(a) preparing a dihydric aromatic compound by a method comprising the steps of:
 (i) introducing into a desorber column possessing a non-aggregate packing material an adduct of a dihydric aromatic compound and phenol;
 (ii) providing an operating temperature range in the desorber column that is sufficiently high and an operating pressure in the column that is sufficiently low such that the adduct is distilled;
 (iii) discharging from the desorber column a first stream containing substantially all of the phenol; and
 (iv) discharging from the desorber column a second stream containing substantially all of the dihydric aromatic compound; whereby the second stream is substantially free of particulate matter added in the desorber column; and
(b) reacting the dihydric aromatic compound from the second stream with a derivative of carbonic acid to form a polycarbonate to form a low-particulate polycarbonate.

16. The method of claim 15, wherein the non-aggregate packing material is selected from the group consisting of borosilicate glass, stainless steel, zirconia, and polytetrafluoroethylene.

17. The method of claim 15, wherein the non-aggregate packing material is made from borosilicate glass.

18. The method of claim 15, wherein a stripping gas is introduced to the column in countercurrent flow to the adduct.

19. The method of claim 18, wherein the operating temperature range in the column is about 172 to about 217° C.

20. The method of claim 18, wherein the operating pressure of the column is in a range from about 35 to about 810 mm Hg.

21. The method of claim 18, wherein the operating pressure of the column is less than atmospheric pressure.

22. The method of claim 18, wherein the stripping gas is selected from the group consisting of nitrogen, carbon dioxide and steam.

23. The method of claim 15, wherein the derivative of carbonic acid is a carbonic diester.

24. The method of claim 23, wherein the carbonic diester is diphenyl carbonate.

25. The method of claim 15, wherein the derivative of carbonic acid is a carbonyl halide.

26. The method of claim 25, wherein the carbonyl halide is carbonyl chloride.

27. The method of claim 15, wherein less than 20,000 particulates per gram of bisphenol are added in the desorber column.

28. A facility for separation of an adduct of a dihydric phenol and phenol into separate streams of dihydric phenol and phenol, comprising a source of the adduct and a desorber column connected to the source of adduct, said desorber column being packed with a non-aggregate packing material.

29. The facility of claim 28, wherein the non-aggregate packing material is selected from the group consisting of borosilicate galls, stainless steel, zirconia and polytetrafluoroethylene.

30. The facility of claim 28, wherein the non-aggregate packing material is made from borosilicate glass.

31. The facility of claim 28, further comprising a source of stripping gas, connected to the desorber column to introduce stripping gas in counter-current flow to the adduct.

32. The facility of claim 31, wherein the source of stripping gas supplies a stripping gas selected from the group consisting of nitrogen, carbon dioxide and steam.

33. The facility of claim 28, wherein the source of adduct supplies an adduct of bisphenol and phenol.

34. The facility of claim 33, wherein the bisphenol is bisphenol-A.

35. The facility of claim 28, further comprising a ring pump connected to the desorber column for maintaining sub-atmospheric pressure in the desorber column during operation.

36. The facility of claim 35, wherein the non-aggregate packing material is selected from the group consisting of borosilicate galls, stainless steel, zirconia and polytetrafluoroethylene.

37. The facility of claim 35, wherein the non-aggregate packing material is made from borosilicate glass.

38. The facility of claim 35, further comprising a source of stripping gas, connected to the desorber column to introduce stripping gas in counter-current flow to the adduct.

39. The facility of claim 38, wherein the source of stripping gas supplies a stripping gas selected from the group consisting of nitrigen, carbon dioxide and steam.

* * * * *